US009408577B2

(12) United States Patent
Tamura et al.

(10) Patent No.: US 9,408,577 B2
(45) Date of Patent: Aug. 9, 2016

(54) MULTIRADIATION GENERATION APPARATUS AND RADIATION IMAGING SYSTEM UTILIZING DUAL-PURPOSE RADIATION SOURCES

(71) Applicant: CANON KABUSHIKI KAISHA, Tokyo (JP)

(72) Inventors: Miki Tamura, Kawasaki (JP); Kazuyuki Ueda, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 179 days.

(21) Appl. No.: 14/189,952

(22) Filed: Feb. 25, 2014

(65) Prior Publication Data

US 2014/0241492 A1  Aug. 28, 2014

(30) Foreign Application Priority Data

Feb. 26, 2013  (JP) ................. 2013-035612

(51) Int. Cl.
*H01J 35/06* (2006.01)
*H01J 35/12* (2006.01)
*H01J 35/16* (2006.01)
*A61B 6/02* (2006.01)
*A61B 6/00* (2006.01)

(52) U.S. Cl.
CPC ............ *A61B 6/025* (2013.01); *A61B 6/4007* (2013.01); *H01J 35/06* (2013.01); *H01J 35/12* (2013.01); *H01J 35/16* (2013.01); *A61B 6/4085* (2013.01); *H01J 2201/30469* (2013.01); *H01J 2235/068* (2013.01); *H01J 2235/166* (2013.01); *H01J 2235/168* (2013.01); *H01J 2235/186* (2013.01); *H01J 2235/205* (2013.01)

(58) Field of Classification Search
CPC ................................. H01J 2235/068
See application file for complete search history.

(56) References Cited

U.S. PATENT DOCUMENTS

| 6,430,264 | B1 * | 8/2002 | Lee | H01J 35/108 378/143 |
| 6,664,463 | B1 * | 12/2003 | Treiber | G06F 1/20 174/383 |
| 6,682,492 | B1 * | 1/2004 | Joensuu | G01R 33/285 600/561 |
| 8,094,773 | B2 | 1/2012 | Boese et al. | |
| 8,149,987 | B2 | 4/2012 | Ogura et al. | |
| 2002/0094064 | A1 * | 7/2002 | Zhou | A61B 6/032 378/122 |
| 2004/0028183 | A1 * | 2/2004 | Lu | A61B 6/4021 378/109 |
| 2006/0049359 | A1 * | 3/2006 | Busta | A23L 3/263 250/370.09 |
| 2006/0182225 | A1 * | 8/2006 | Besson | A61B 6/025 378/146 |
| 2010/0166141 | A1 * | 7/2010 | Vermilyea | H01J 35/10 378/19 |

(Continued)

FOREIGN PATENT DOCUMENTS

| CN | 1891017 A | 1/2007 |
| CN | 1953219 A | 4/2007 |

(Continued)

*Primary Examiner* — Nicole Ippolito
*Assistant Examiner* — Sean Luck
(74) *Attorney, Agent, or Firm* — Canon U.S.A., Inc., IP Division

(57) ABSTRACT

A multiradiation generation apparatus according to the present invention includes a plurality of radiation sources arranged in a row. Each of the radiation sources includes an electron source configured to emit electrons and a target unit configured to generate radiation upon receiving electrons emitted from the electron source. At least one of the radiation sources is a dual-purpose radiation source used for both tomosynthesis imaging and non-tomosynthesis imaging, and the other radiation sources are single-purpose radiation sources used only for tomosynthesis imaging.

26 Claims, 10 Drawing Sheets

(56) References Cited

U.S. PATENT DOCUMENTS

| | | | |
|---|---|---|---|
| 2010/0189223 A1* | 7/2010 | Eaton | G21K 1/025 378/68 |
| 2011/0007874 A1* | 1/2011 | Vogtmeier | H01J 1/3048 378/119 |
| 2011/0103554 A1* | 5/2011 | Charette | G01V 5/0041 378/138 |
| 2011/0188625 A1* | 8/2011 | Roshi | H01J 35/06 378/4 |
| 2012/0057669 A1 | 3/2012 | Vogtmeier | |
| 2012/0195403 A1 | 8/2012 | Vedantham | |

FOREIGN PATENT DOCUMENTS

| | | |
|---|---|---|
| CN | 101219056 A | 7/2008 |
| CN | 101395691 A | 3/2009 |
| CN | 102792782 A | 11/2012 |
| DE | 102010062541 A1 | 6/2012 |
| JP | 2008-067933 A | 3/2008 |

\* cited by examiner

MULTIRADIATION GENERATION APPARATUS AND RADIATION IMAGING SYSTEM UTILIZING DUAL-PURPOSE RADIATION SOURCES

BACKGROUND OF THE INVENTION

1. Field of the Invention

The present invention relates to a multiradiation generation apparatus, which is applicable to, for example, nondestructive X-ray imaging used in the fields of medical equipment and industrial equipment, and to a radiation imaging system using the multiradiation generation apparatus.

2. Description of the Related Art

In recent years, in the field of radiation imaging such as mammography, tomosynthesis imaging has been performed as a technique for obtaining information on the depth direction of an object. In tomosynthesis imaging, an object is irradiated with radiation from a plurality of angles to capture a plurality of images. The obtained images are reconstructed to obtain a cross-sectional image.

Normally, in tomosynthesis imaging, an operator performs imaging by irradiating an object with radiation while moving radiation tubes at an angle within a predetermined angle range (approximately ±7.5° to ±25°) with respect to the object.

U.S. Pat. No. 8,094,773 discusses a three-dimensional X-ray image generation device. By using a plurality of X-ray sources and sequentially irradiating an object with the X rays from a plurality of angles, this device performs tomosynthesis imaging while maintaining the X-ray sources in a fixed state. In addition, there is discussed a device including non-tomosynthesis imaging X-ray sources outside a tomosynthesis imaging path, in addition to tomosynthesis imaging X-ray sources.

The apparatus that involves the movement of the radiation tubes during imaging has problems. For example, artifacts are formed on images. In addition, since time is required for the mechanical movement, imaging time is prolonged. In addition, movement of the radiation tubes could give a subject a sense of fear.

In clinical practice, there are cases in which both tomosynthesis images and conventional two-dimensional (2D) images (non-tomosynthesis images) are used. These 2D images are advantageous since the 2D images can provide higher spatial resolution than that of tomosynthesis images and medical professionals can make use of years of knowledge. Thus, it is effective to use tomosynthesis images for specifically observing a portion that seems suspicious on 2D images.

However, if tomosynthesis imaging radiation sources and non-tomosynthesis imaging radiation sources are separately provided, the configurations of the apparatuses are made complex, thereby increasing manufacturing costs of the apparatuses. In addition, the tomosynthesis images and non-tomosynthesis images need to be appropriately associated with each other. Thus, the positional relationship among the tomosynthesis imaging radiation sources and the non-tomosynthesis imaging radiation sources needs to be optimized, which is a layout constraint.

SUMMARY OF THE INVENTION

The present invention is directed to a multiradiation generation apparatus applicable to both tomosynthesis imaging and non-tomosynthesis imaging with a simpler configuration and a radiation imaging system using the multiradiation generation apparatus.

According to an aspect of the present invention, a multiradiation generation apparatus includes a plurality of radiation sources arranged in a row. Each of the radiation sources includes an electron source configured to emit electrons and a target unit configured to generate radiation upon receiving electrons emitted from the electron source. At least one of the radiation sources is a dual-purpose radiation source used for both tomosynthesis imaging and non-tomosynthesis imaging, and the other radiation sources are single-purpose radiation sources used only for tomosynthesis imaging.

Further features of the present invention will become apparent from the following description of exemplary embodiments with reference to the attached drawings.

BRIEF DESCRIPTION OF THE DRAWINGS

FIG. 1A is a front vertical sectional view, FIG. 1B is a bottom view, and FIG. 1C is an enlarged sectional view near a dual-purpose radiation source.

FIG. 2A is a front vertical sectional view, FIG. 2B is a bottom view, and FIG. 2C is an enlarged sectional view near a dual-purpose radiation source.

FIG. 4A is a front vertical sectional view and FIG. 4B is a bottom view.

FIG. 5A is a front vertical sectional view and FIG. 5B is a bottom view.

FIGS. 6A and 6B are schematic sectional views illustrating configurations of shields.

FIG. 9A illustrates a tomosynthesis imaging method and FIG. 9B illustrates a non-tomosynthesis imaging method.

DESCRIPTION OF THE EMBODIMENTS

Various exemplary embodiments, features, and aspects of the invention will be described in detail below with reference to the drawings. While X-rays can be used as radiation in exemplary embodiments, other kinds of radiation such as neutron rays or proton beams are also applicable. In addition, hereinafter, a multiradiation generation apparatus 1 will simply be referred to as a radiation generation apparatus 1 and a multi-electron source 4 will simply be referred to as an electron source 4.

Figure 1A:
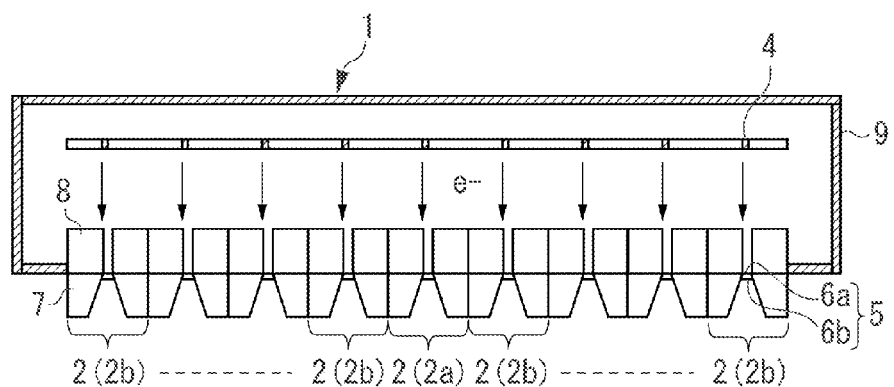
FIGS. 1A, 1B, and 1C illustrate a multiradiation generation apparatus according to a first exemplary embodiment. More specifically.
Figure 1B:
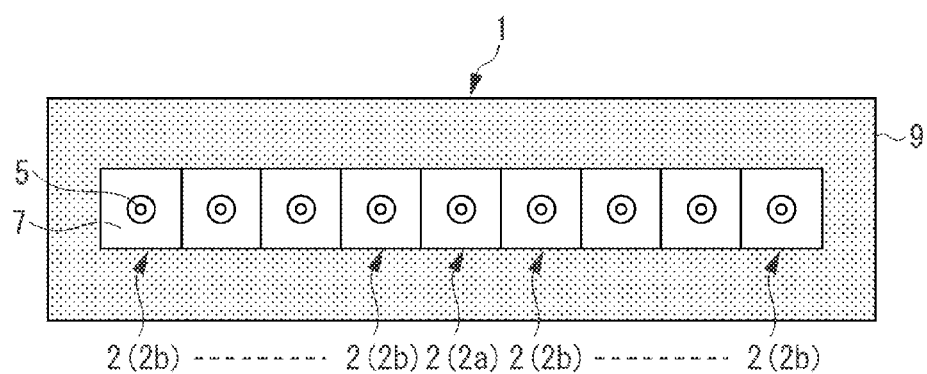
Figure 1C:
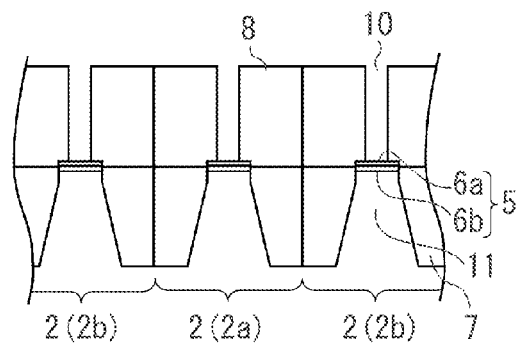

As illustrated in FIGS. 1A, 1B, and 1C, a radiation generation apparatus 1 according to a first exemplary embodiment includes a plurality of radiation sources 2, each of which has an electron source 4 emitting electrons and a target unit 5 generating radiation when electrons are emitted. In addition, the radiation generation apparatus 1 includes a vacuum case 9. The electron sources 4 and target units 5 are lined up at intervals. Namely, the radiation sources 2 are arranged in a row. Among the radiation sources 2, a radiation source used for both tomosynthesis imaging and non-tomosynthesis imaging will hereinafter be referred to as a dual-purpose radiation source 2a. In contrast, radiation sources used only for tomosynthesis imaging will hereinafter be referred to as single-purpose radiation sources 2b. While only one dual-purpose radiation source 2a can be arranged as the center radiation source, if the radiation dose is insufficient, a plurality of radiation sources 2 may be used as the dual-purpose radiation sources 2a. If a plurality of dual-purpose radiation sources 2a is arranged, the number of dual-purpose radiation sources 2a can be set to equal to or less than one-tenth of the total number of radiation sources 2, to achieve reduction of the apparatus cost. In particular, the number of dual-purpose radiation sources 2a can be set to three or less. In addition, the dual-purpose radiation source 2a can be arranged at the center in the row of the radiation sources 2, to facilitate irradiation of radiation to a necessary region during non-tomosynthesis imaging.

Each target unit 5 includes a target layer 6a and a substrate 6b, and the target layer 6a is formed on the substrate 6b on the side which faces a corresponding electron source 4. When electrons emitted from an electron source 4 are caused to be incident on a target layer 6a of a target 5, radiation is generated from the target layer 6a. The generated radiation is emitted to the outside of the radiation generation apparatus 1 through a corresponding substrate 6b.

The inside of the radiation generation apparatus 1 is maintained to be under a reduced-pressure atmosphere. The degree of vacuum inside the radiation generation apparatus 1 is at least within the range between approximately $10^{-4}$ to $10^{-8}$ Pa. The reduced-pressure atmosphere can be formed by providing the vacuum case 9 with an exhaust tube (not illustrated). To maintain a necessary degree of vacuum, a getter (not illustrated) may be arranged inside the radiation generation apparatus 1.

For each electron source 4, a hot cathode such as a tungsten filament or an impregnated cathode, or a cold cathode such as a carbon nanotube can be used. An extraction electrode (not illustrated) and a lens electrode (not illustrated) may be arranged near the electron source 4 of each radiation source 2. The extraction electrode and the lens electrode are arranged in this order between the corresponding electron source 4 and the corresponding target unit 5. If these electrodes are arranged, emission of electrons from the electron source 4 is promoted by the electric field formed by the extraction electrode, and the emitted electrons are converged by the lens electrode and are caused to be incident on the target unit 5.

A material having a high melting point and high radiation generation efficiency can be used as a material of each target layer 6a. For example, a material such as tungsten, tantalum, molybdenum, or an alloy of these materials can be used. Each target layer 6a can be formed to have a thickness of 1 to 20 μm.

As a material of each substrate 6b, a material supporting the target layer 6a and having sufficient strength for sealing the inside of the radiation generation apparatus 1 can be used. In addition, a material absorbing less radiation generated from the target layer 6a and having high thermal conductivity can be used so that heat generated from the target layer 6a can be released quickly. For example, diamond, silicon carbide, and aluminum nitride can be used.

Shields 7 and 8 can be arranged around the target unit 5 of each radiation source 2. When radiation is emitted from the target layer 6a, these shields 7 and 8 shield unnecessary radiation. Each shield 8, which is arranged closer to a corresponding electron source 4 than each shield 7 is, is in communication with a corresponding target layer 6a, and has a passage hole 10 through which electrons emitted from the electron source 4 pass. Each shield 7, which is arranged farther from the electron source 4 than each shield 8 is, has an emission hole 11 that determines the emission direction (the central axis direction) and the emission angle of radiation emitted from a corresponding target layer 6a to the outside.

The electrons emitted from each electron source 4 pass through the passage hole 10 of a corresponding shield 8 and are emitted to a corresponding target layer 6a. Each shield 8 shields the radiation and the reflected electrons scattered by a corresponding target layer 6a in the direction of a corresponding electron source 4. In addition, the radiation that has passed through a corresponding substrate 6b passes through the emission hole 11 of a corresponding shield 7. The radiation traveling in unnecessary directions is shielded by the shield 7 and is emitted to a predetermined region via the emission hole 11. As a material of the shields 7 and 8, a material having high radiation absorption and high thermal conductivity can be used. For example, a metal material such as tungsten, tantalum, or copper can be used. In FIGS. 1A, 1B, and 1C, the shields 7 and 8 arranged for each radiation source 2 are illustrated separately. However, these shields 7 and 8 can be formed integrally to improve the heat conductivity of the shields 7 and 8 as a whole.

In tomosynthesis imaging, radiation is emitted to a single region on an irradiated surface of an object from different angles. Namely, the object is irradiated with radiation from a plurality of angles. The number of angles is equal to the number of radiation sources 2 each including a combination of an electron source 4 and a target layer 6a. Each emission hole 11 is formed so that radiation emitted from a corresponding target layer 6a is emitted to a single region on an irradiated surface. Namely, each emission hole 11 is formed so that the direction of the central axis of each columnar emission hole 11 varies depending on the position of each emission hole 11. For example, assuming that the central axis of an emission hole 11 arranged in the center of the row of the radiation sources 2 matches the axis along which an electron beam passes, the central axis of an emission hole 11 formed closer to both ends of the row of the radiation sources 2 is formed to be inclined toward the center. As a result, the central axes of cone-beam-shaped radiation emitted from all radiation sources can intersect at a single point on an irradiated surface.

The shield 8 and the shield 7 can be formed integrally.

Figure 2A:
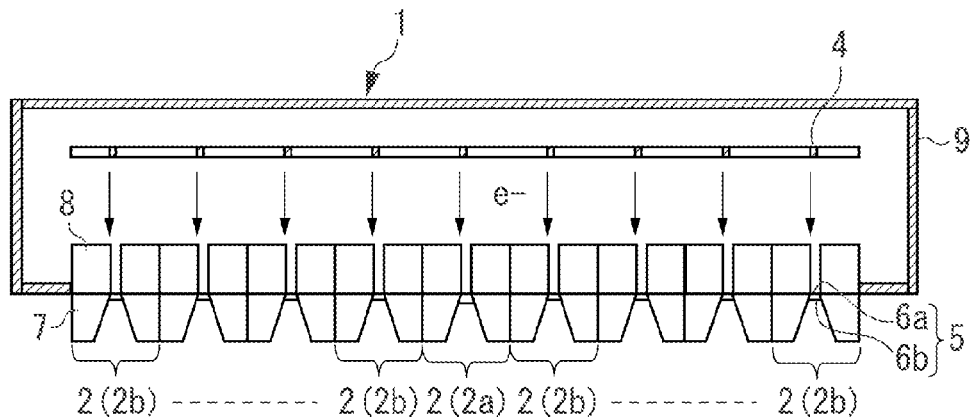
FIGS. 2A, 2B, and 2C illustrate a multiradiation generation apparatus according to a second exemplary embodiment. More specifically.
Figure 2B:
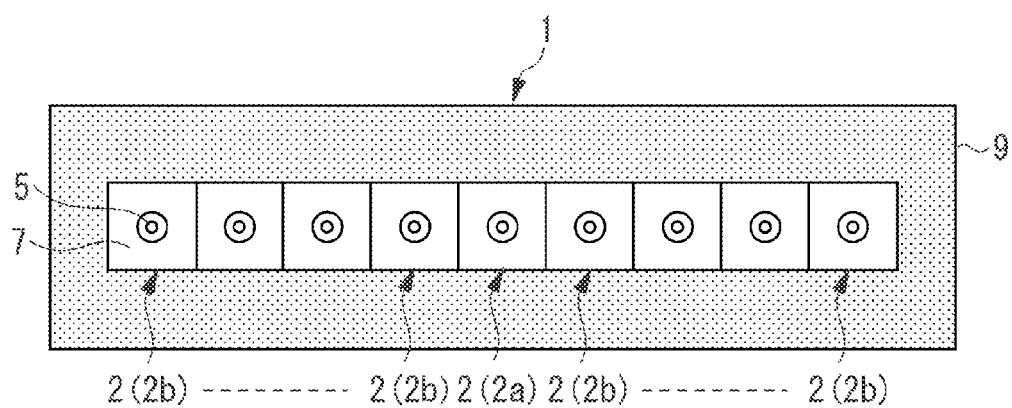
Figure 2C:
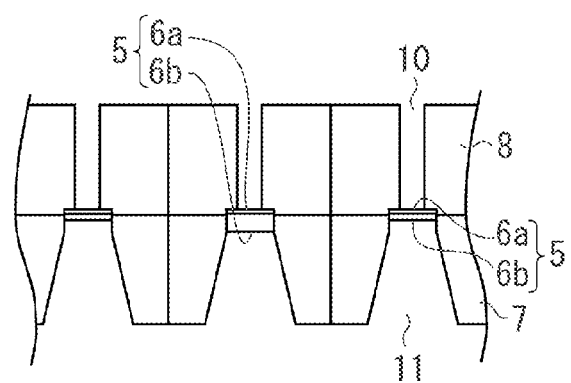

A basic configuration according to a second exemplary embodiment is similar to that according to the first exemplary embodiment. However, when electrons are irradiated under the same conditions, the electron irradiated surface of the target unit 5 of the dual-purpose radiation source 2a experiences a smaller temperature increase than that experienced by the electron irradiated surfaces of the target units 5 of the single-purpose radiation sources 2b. More specifically, as illustrated in FIG. 2C, the substrate 6b of the target unit 5 of the dual-purpose radiation source 2a is formed to be thicker than the substrates 6b of the target units 5 of the single-purpose radiation sources 2b.

When electrons are caused to be incident on a target layer 6a, most of the incident energy is converted into heat. Thus, the number of electrons (current amount) that can be caused to be incident on a target layer 6a is limited by heat resistance and heat release properties of the target layer 6a. In the present exemplary embodiment, the heat generated by each target layer 6a is released to the outside of the radiation generation apparatus 1 via a corresponding substrate 6b and corresponding shields 7 and 8. Since the substrate 6b of the dual-purpose radiation source 2a is thicker than the substrates 6b of the single-purpose radiation sources 2b, which are the other radiation sources 2, the heat generated by the target layer 6a is transmitted to the shields 7 and 8 more quickly via the substrate 6b. Thus, when electrons are emitted to a target layer 6a under the same conditions, the target layer 6a, which is an electron irradiated surface, experiences a smaller temperature increase than that of the target layers 6a of the single-purpose radiation sources 2b. As a result, a larger current amount can be caused to be incident on the target layer 6a.

Generally, the substrate 6b can be formed to have a thickness of 0.05 to 10 mm. The thickness of the substrate 6b of the target unit 5 of the dual-purpose radiation source 2a according to the present exemplary embodiment varies depending on a material of the substrate 6b. However, within the above thickness range, the thickness can be set to approximately 1.5 to 5 times the thickness of the substrates 6b of the target units 5 of the single-purpose radiation sources 2b. The substrates 6b of all the radiation sources 2 can be formed to have the same thickness as that of the substrate 6b of the dual-purpose radiation source 2a. However, by increasing only the thickness of the substrate 6b of the dual-purpose radiation source 2a, an unnecessary increase in manufacturing cost can be avoided.

According to the present exemplary embodiment, a larger current amount can be supplied to the target unit 5 of the dual-purpose radiation source 2a than the current amount that can be supplied to the target units 5 of the single-purpose radiation sources 2b.

Figure 3:
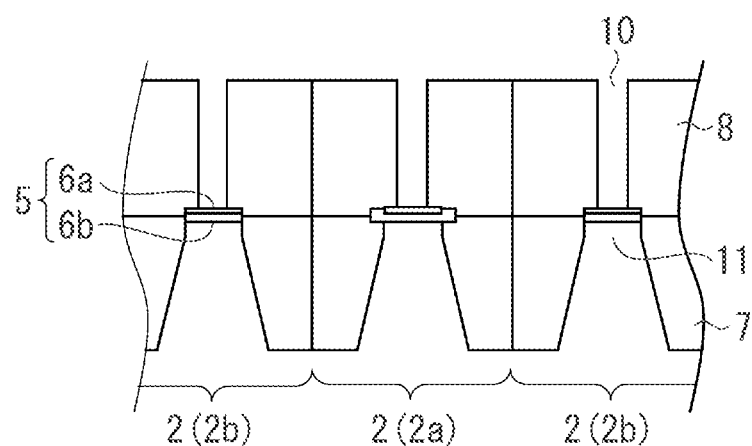
FIG. 3 is a schematic sectional view of a target unit of a dual-purpose radiation source according to a third exemplary embodiment.

FIG. 3 illustrates another configuration for making the temperature increase of the electron irradiated surface of the target unit 5 of the dual-purpose radiation source 2a according to a third exemplary embodiment smaller than that of each of the electron irradiated surfaces of the target units 5 of the single-purpose radiation sources 2b when electrons are irradiated under the same conditions. The diameter of the substrate 6b of the dual-purpose radiation source 2a is formed to be larger than that of each of the substrates 6b of the single-purpose radiation sources 2b. As described above, diamond, silicon carbide, aluminum nitride, or the like can be used as a material of each substrate 6b. These materials have higher thermal conductivity than that of metal materials of the shields 7 and 8. Thus, by increasing the diameter of the substrate 6b, the heat release properties of the target layer 6a can be increased, whereby a larger current amount can be caused to be incident on the target layer 6a.

An optimum range of the diameter of the substrate 6b can be determined based on the focus diameter of radiation, the intervals of the radiation sources 2, the manufacturing cost and the manufacturing workability of the substrate 6b, or the like. Generally, the diameter can be set to approximately 1 to 10 mm. The diameter of the substrate 6b of the dual-purpose radiation source 2a varies depending on a material of the substrate 6b. Generally, the diameter can be set to approximately 1.5 to 5 times the diameter of each of the substrates 6b of the single-purpose radiation sources 2b. The substrates 6b of all the radiation sources 2 can be formed to have the same diameter as that of the substrate 6b of the dual-purpose radiation source 2a. However, by increasing only the diameter of the substrate 6b of the dual-purpose radiation source 2a, an unnecessary increase in manufacturing cost can be avoided.

Figure 4A:
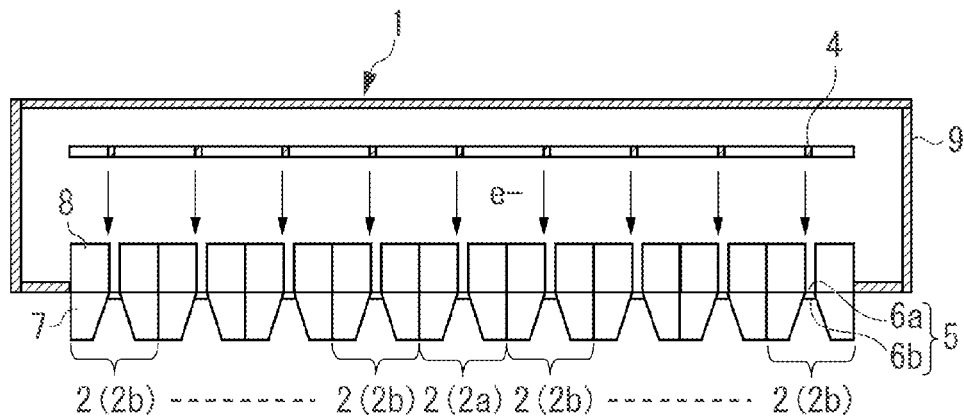
FIGS. 4A and 4B illustrate a multiradiation generation apparatus according to a fourth exemplary embodiment. More specifically.
Figure 4B:
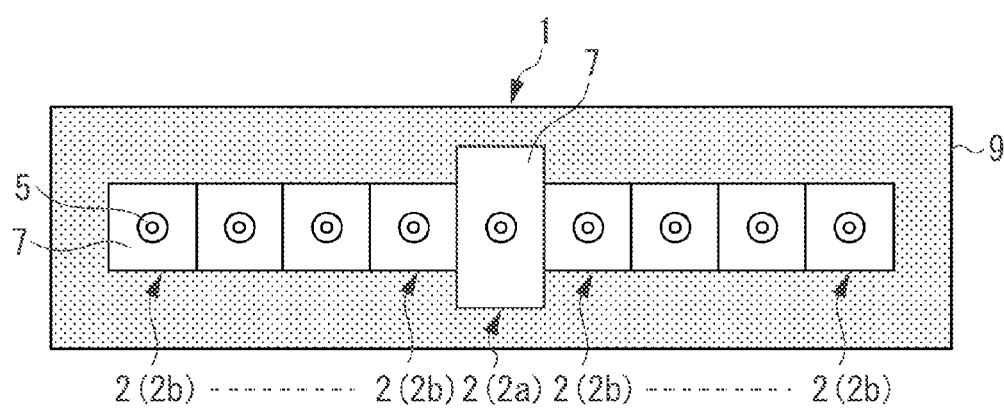

A basic configuration according to a fourth exemplary embodiment is similar to that according to the first exemplary embodiment. However, as illustrated in FIGS. 4A and 4B, the shields 7 and 8 of the dual-purpose radiation source 2a are formed to be thicker than the shields 7 and 8 of the single-purpose radiation sources 2b in a direction perpendicular to the row of the target units 5 and to the direction in which electrons are caused to be incident. The heat generated by each target layer 6a is released to the outside of the radiation generation apparatus 1 via a corresponding substrate 6b and corresponding shields 7 and 8. By increasing the thickness of the shields 7 and 8 of the dual-purpose radiation source 2a as described above, the heat is isotropically and widely diffused. Namely, the heat release properties are improved. In addition, since the heat capacities of the shields 7 and 8 are increased, the temperature increase is reduced. Thus, a larger current amount can be caused to be incident on the target layer 6a.

The thickness of the shields 7 and 8 of the dual-purpose radiation source 2a in the direction perpendicular to the row of the target units 5 and to the direction in which electrons are caused to be incident can be set to be a larger value than a distance L by which the heat generated by the target layer 6a is transferred (a heat transfer distance L). This heat transfer distance L is represented by the following Formula (1).

$$L = \{(t \times \lambda)/(C \times \rho)\}^{0.5} \quad (1)$$

The heat transfer distance L is calculated by using an average imaging time t during non-tomosynthesis imaging, a thermal conductivity $\lambda$ of the shields 7 and 8, a specific heat C of the shields 7 and 8, and a density $\rho$ of the shields 7 and 8.

The shields 7 and 8 of all the radiation sources 2 can be formed to be thicker in the direction perpendicular to the row of the target units 5 and to the direction in which electrons are caused to be incident. However, by increasing only the thickness of the shields 7 and 8 of the dual-purpose radiation source 2a, unnecessary increases in manufacturing cost and weight can be avoided.

Figure 5A:
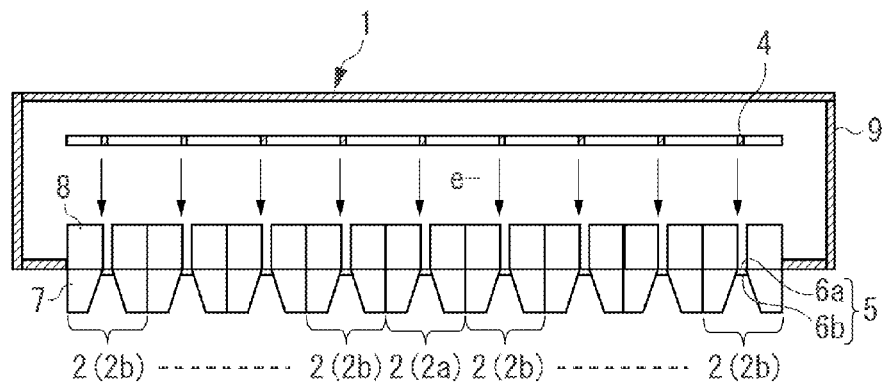
FIGS. 5A and 5B illustrate a multiradiation generation apparatus according to a fifth exemplary embodiment. More specifically.
Figure 5B:
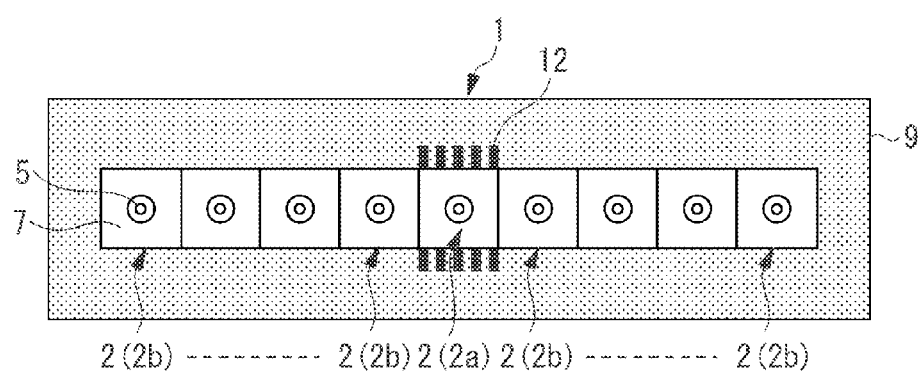

A basic configuration according to a fifth exemplary embodiment is similar to that according to the first exemplary embodiment. However, as illustrated in FIGS. 5A and 5B, a heat release fin 12 is connected to the shields 7 and 8 of the dual-purpose radiation source 2a. The fin 12 can be arranged on surfaces of the shields 7 and 8 and at least on an outer side of the vacuum case 9.

By connecting the fin 12 to the shields 7 and 8 of the dual-purpose radiation source 2a, the heat release properties of the shields 7 and 8 are increased, and the temperature increase of the target layer 6a is further reduced. Thus, a larger current amount can be caused to be incident on the target layer 6a.

A material such as copper or aluminum can be used as a material of the fin 12. In addition, the fin 12 can be integrally formed with the shields 7 and 8. The shields 7 and 8 of all the radiation sources 2 can be connected to respective fins 12. However, by connecting a fin 12 only to the shields 7 and 8 of the dual-purpose radiation source 2a, unnecessary increases in manufacturing cost and weight can be avoided.

Figure 6A:
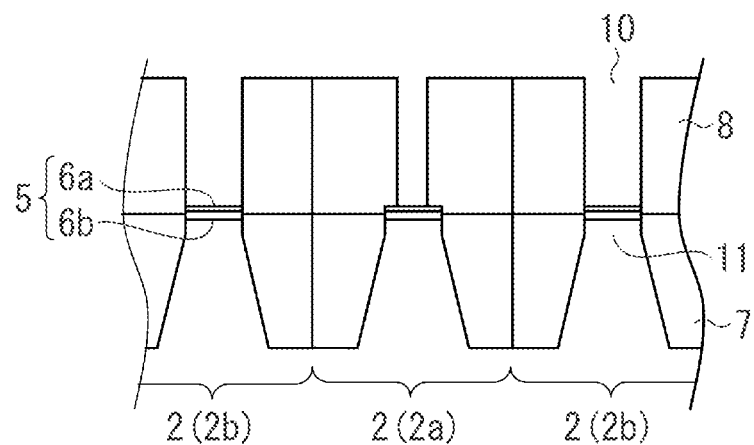
FIGS. 6A and 6B illustrate configurations around a target unit of a dual-purpose radiation source according to a sixth exemplary embodiment. More specifically.
Figure 6B:
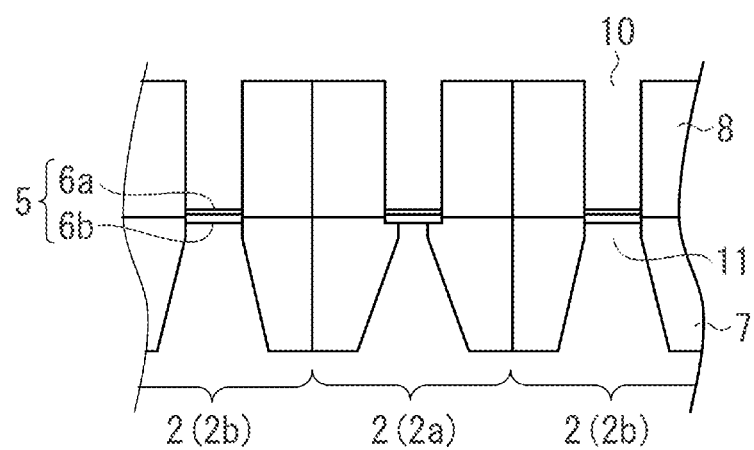

In FIG. 6A, the passage hole 10 of the shield 8 of the dual-purpose radiation source 2a according to a sixth exemplary embodiment has a smaller diameter at a place where the passage hole 10 is in contact with the target unit 5 than that of each of the passage holes 10 of the shields 8 of the single-purpose radiation sources 2b. In FIG. 6B, the emission hole 11 of the shield 8 of the dual-purpose radiation source 2a has a smaller diameter at a place where the emission hole 11 is in contact with the target unit 5 than that of each of the emission holes 11 of the shields 8 of the single-purpose radiation sources 2b. Alternatively, the shield 8 of the dual-purpose radiation source 2a can be formed to have both configurations in FIGS. 6A and 6B.

As for the dual-purpose radiation source 2a, the distance between the position of the target layer 6a to which electrons are emitted (a heat generation position) and a corresponding shield 7 and/or a corresponding shield 8 is reduced. Thus, since the heat generated by the target layer 6a is quickly transmitted to the shield 7 and/or the shield 8, the heat release properties of the target layer 6a is further increased. As a result, a larger current amount can be caused to be incident on the target layer 6a.

Appropriate values are set for the diameter of the passage hole 10 and the diameter of the emission hole 11, based on the focus diameter, the shielding properties for unnecessary radiation, the accuracy of the alignment between the electron source 4 and the radiation source 2, for example. If the diameter of the passage hole 10 and/or the emission hole 11 is reduced, high accuracy is required for the alignment between the electron source 4 and the radiation source 2. Thus, the diameter of the passage hole 10 and/or the emission hole 11 can be reduced only for the dual-purpose radiation source 2a. In this way, highly accurate alignment is required only for the dual-purpose radiation source 2a.

Figure 7:
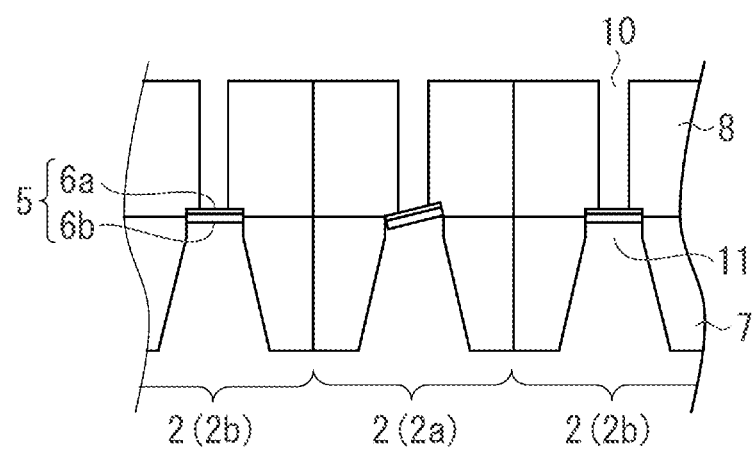
FIG. 7 is a schematic sectional view illustrating an installation configuration of a target unit according to a seventh exemplary embodiment.

The target unit 5 of the dual-purpose radiation source 2a according to a seventh exemplary embodiment illustrated in FIG. 7 is arranged with an inclination with respect to the direction in which electrons are caused to be incident. In addition, the target units 5 of the single-purpose radiation sources 2b, which are the other radiation sources 2, are arranged perpendicular to the direction in which electrons are caused to be incident. By arranging the target unit 5 with an inclination with respect to the direction in which electrons are caused to be incident, the density of current per unit area that is caused to be incident on the target unit 5 can be reduced. Thus, a larger current amount can be caused to be incident on the target unit 5. The target unit 5 of the dual-purpose radiation source 2a can be arranged with an inclination of approximately 30° to 60° with respect to the direction in which electrons are caused to be incident. The target units 5 of all the radiation sources 2 can be arranged with an inclination, as is the case with the target unit 5 of the dual-purpose radiation source 2a. However, by arranging only the target unit 5 of the dual-purpose radiation source 2a with an inclination, an unnecessary increase in manufacturing cost can be avoided.

An eighth exemplary embodiment relates to a radiation imaging system in which a radiation generation apparatus described in the first to seventh exemplary embodiments is applied.

Figure 8:
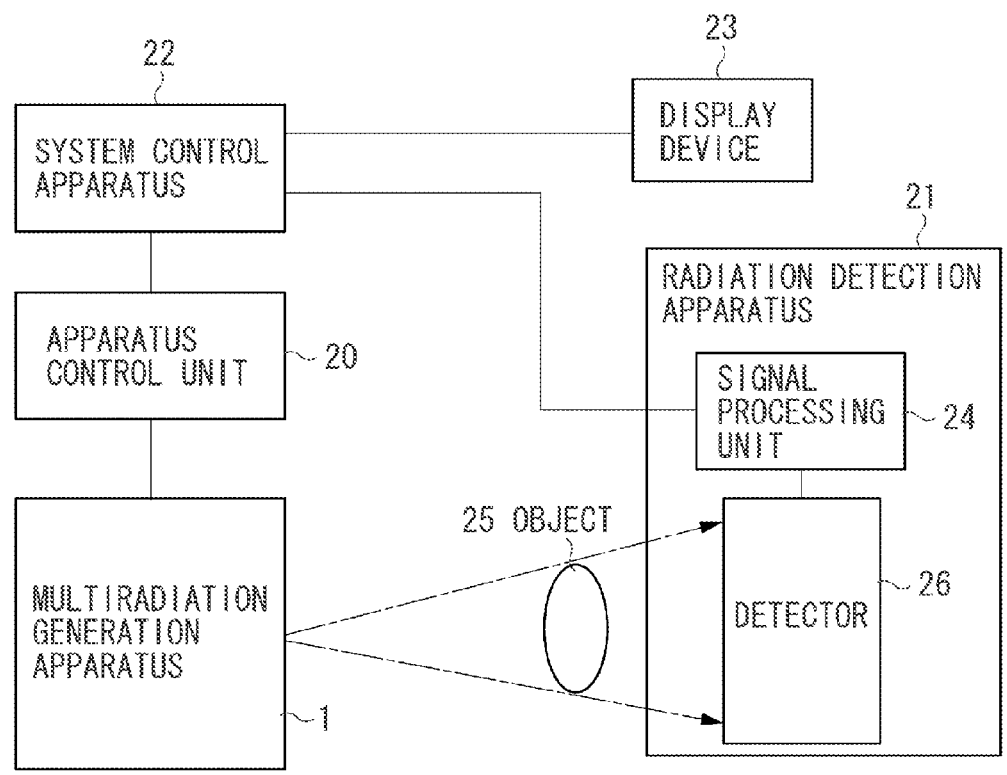
FIG. 8 illustrates a configuration of a radiation imaging system according to an eighth exemplary embodiment.

FIG. 8 illustrates a configuration of the radiation imaging system. A system control apparatus 22 performs cooperation control over the radiation generation apparatus 1 and a radiation detection apparatus 21. Under the control of the system control apparatus 22, an apparatus control unit 20 outputs various control signals to the radiation generation apparatus 1. These control signals control statuses of radiation emitted from the radiation generation apparatus 1. The radiation emitted from the radiation generation apparatus 1 passes through an object 25 and is detected by a detector 26. The radiation detection apparatus 21 converts the detected radiation into image signals and outputs the image signals to a signal processing unit 24. Under the control of the system control apparatus 22, the signal processing unit 24 performs predetermined signal processing on the image signals and outputs processed image signals to the control apparatus 22. Based on the processed image signals, the system control apparatus 22 outputs, to a display device 23, display signals for causing the display device 23 to display images. Based on the display signals, the display device 23 displays images on a screen as captured images of the object 25.

Next, tomosynthesis imaging and non-tomosynthesis imaging using the radiation imaging system according to the present exemplary embodiment will be described with reference to FIGS. 9A and 9B. The radiation imaging system has a tomosynthesis imaging mode and a non-tomosynthesis imaging mode. In the tomosynthesis imaging mode, radiation is sequentially emitted from radiation sources 2 which are arranged in a row (for example, see FIGS. 1A, 1B, and 1C). In the non-tomosynthesis imaging mode, radiation is emitted only from a dual-purpose radiation source 2a (for example, see FIGS. 1A, 1B, and 1C).

Figure 9A:
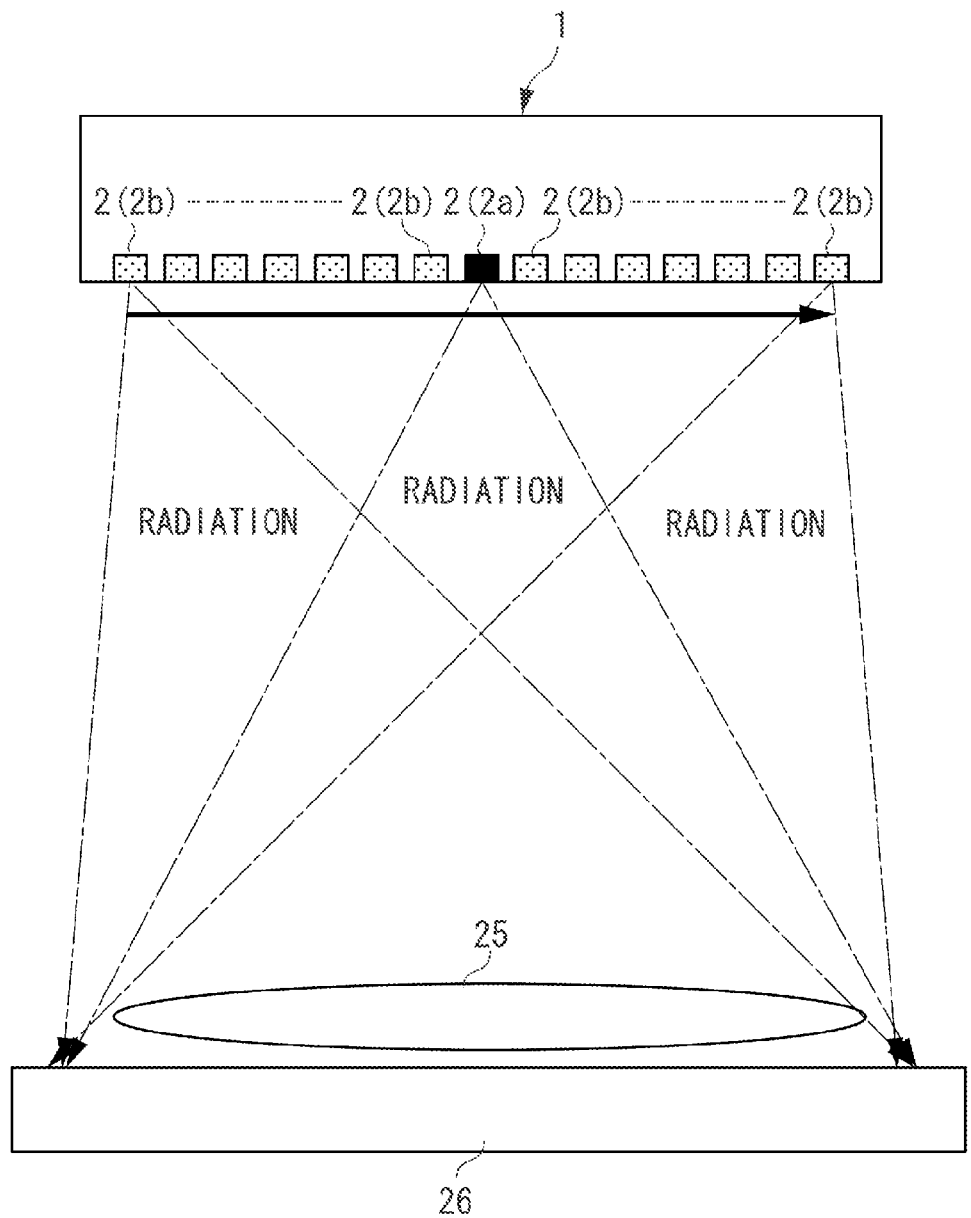
FIGS. 9A and 9B illustrate imaging methods using the radiation imaging system according to the eighth exemplary embodiment of the present invention. More specifically.
Figure 9B:
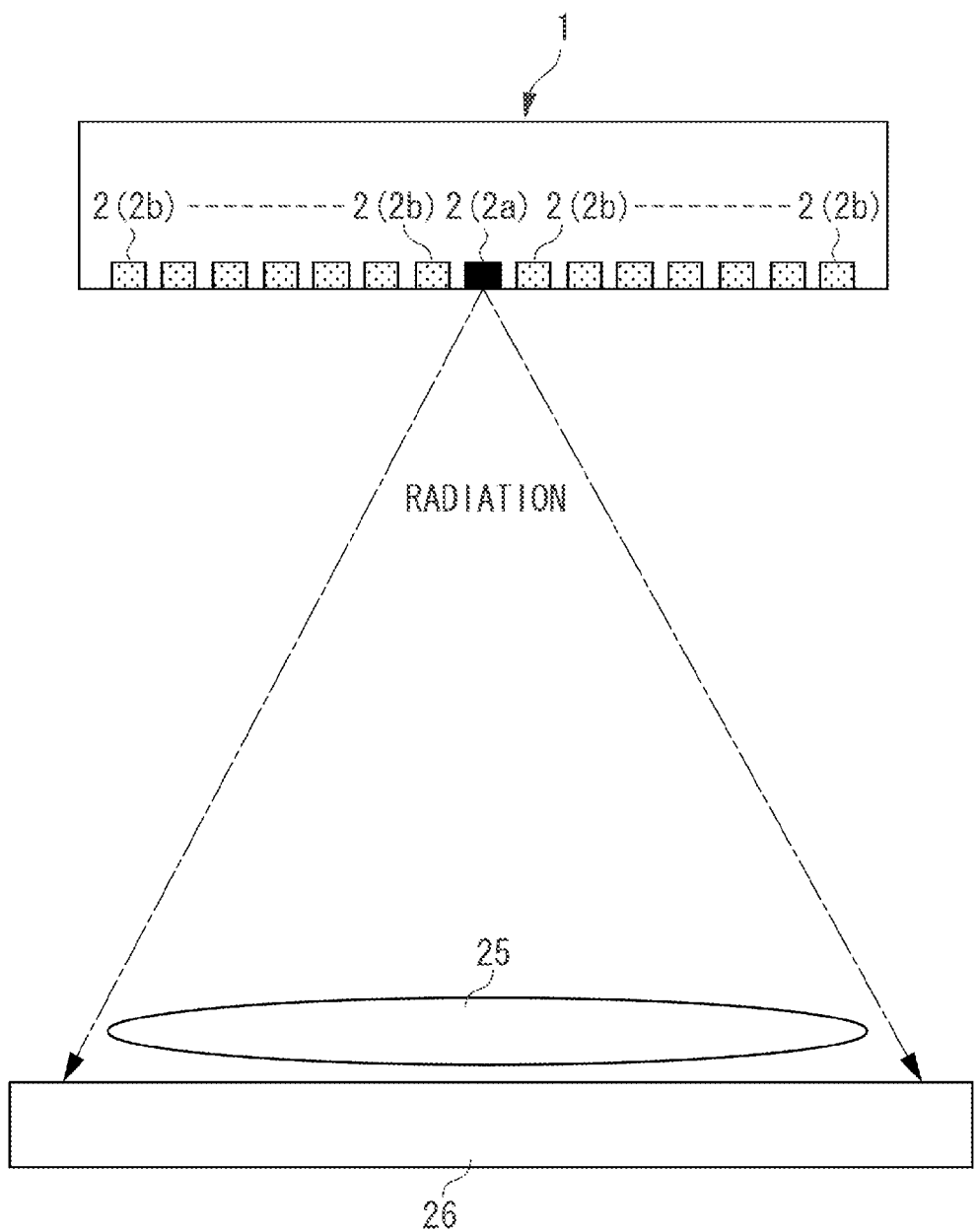

As illustrated in FIG. 9A, in the tomosynthesis imaging mode, radiation is sequentially emitted to the object 25 from the plurality of radiation sources 2 including the dual-purpose radiation source 2a illustrated in FIGS. 1A, 1B, and 1C, for example. The radiation that has passed through the object 25 is detected by the detector 26, and a plurality of images are captured. The plurality of captured images are reconstructed by the signal processing unit 24 and a cross-sectional image is formed. As illustrated in FIG. 9B, in the non-tomosynthesis imaging mode, radiation is emitted to the object 25 from the dual-purpose radiation source 2a. The radiation that has passed through the object 25 is detected by the detector 26, and the signal processing unit 24 forms a 2D image.

The radiation imaging system according to the present exemplary embodiment can continually perform tomosynthesis imaging and non-tomosynthesis imaging, without changing the positions of the radiation sources 2. In addition, the dual-purpose radiation source 2a used for both types of imaging is configured to supply a larger current amount to a corresponding target unit 5 than that of each of the single-purpose radiation sources 2b. Thus, imaging time can be reduced. The amount of current supplied to a target unit 5 can be adjusted by causing the system control apparatus 22 to control an acceleration voltage applied between a corresponding electron source 4 and a corresponding target unit 5. For example, in the tomosynthesis imaging mode, a first acceleration voltage is applied between the electron source 4 and the target unit 5 of each radiation source 2. In contrast, in the non-tomosynthesis imaging mode, a second acceleration voltage different from the first acceleration voltage is applied between the electron source 4 and the target unit 5 of the dual-purpose radiation source 2a. By setting a larger value to the second acceleration voltage than that of the first acceleration voltage, a larger current amount can be supplied to the target unit 5 of the dual-purpose radiation source 2a than that supplied to each of the target units 5 of the single-purpose radiation sources 2b.

In addition, by arranging an extraction electrode (not illustrated) between an electron source 4 and a target unit 5 and causing the system control apparatus 22 to control the voltage applied to the extraction electrode, the amount of current supplied to the target unit 5 can be adjusted. For example, in the tomosynthesis imaging mode, a first voltage is applied between the electron source 4 and the extraction electrode of each radiation source 2. In contrast, in the non-tomosynthesis imaging mode, a second voltage different from the first voltage is applied between the electron source 4 and the extraction electrode of the dual-purpose radiation source 2a. By setting a larger value to the second voltage than that of the first voltage, a larger current amount can be supplied to the target unit 5 of the dual-purpose radiation source 2a than that supplied to each of the target units 5 of the single-purpose radiation sources 2b.

According to the exemplary embodiments of the present invention, by configuring at least one of a plurality of radiation sources as a dual-purpose radiation source, a radiation generation apparatus having a smaller size can be manufactured. In addition, since the dual-purpose radiation source is arranged at a position where the dual-purpose radiation source can be used for both non-tomosynthesis imaging and tomosynthesis imaging, tomosynthesis imaging and non-tomosynthesis imaging can be performed continually without changing the positions of the radiation sources.

Generally, the total radiation dose in tomosynthesis imaging is approximately equal to that in non-tomosynthesis imaging. Thus, for example, when a single dual-purpose radiation source is used, the radiation dose emitted from this dual-purpose radiation source during non-tomosynthesis imaging is at least ten times to several tens of times that emitted from a single radiation source during tomosynthesis imaging. As a result, in non-tomosynthesis imaging, more imaging time is required for obtaining necessary radiation dose.

According to the exemplary embodiments of the present invention, the electron irradiated surface of the target unit of the dual-purpose radiation source is configured to experience a smaller temperature increase than that experienced by each of the target units of the single-purpose radiation sources that only emit radiation for tomosynthesis imaging, when electrons are irradiated under the same conditions. In this way, a larger current amount can be supplied to the target unit of the dual-purpose radiation source during non-tomosynthesis imaging and the generated radiation dose can be increased. As a result, the imaging time can be shortened.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-035612 filed Feb. 26, 2013, which is hereby incorporated by reference herein in its entirety.

What is claimed is:

1. A multiradiation generation apparatus comprising:
a plurality of radiation sources arranged in a row,
wherein at least one of the plurality of radiation sources is a dual-purpose radiation source and the remaining plurality of radiation sources are single-purpose radiation sources,
wherein the dual-purpose radiation source is used for both tomosynthesis imaging and non-tomosynthesis imaging, and the single-purpose radiation sources are used only for tomosynthesis imaging
wherein each of the plurality of radiation sources includes an electron source configured to emit electrons and a target unit configured to generate radiation upon receiving electrons emitted from the electron source,
wherein each of the plurality of radiation sources further includes a shield arranged around the corresponding target unit,
wherein the shield has a passage hole and an emission hole, and
wherein the passage hole or the emission hole of the shield of the dual-purpose radiation source has a smaller diameter at a place where the passage hole or the emission hole is in contact with the target unit than that of each of the passage holes or the emission holes of the shields of the single-purpose radiation sources.

2. The multiradiation generation apparatus according to claim 1, wherein, when electrons are irradiated under the same conditions, an electron irradiated surface of the target unit of the dual-purpose radiation source is configured to have a smaller temperature increase than that of each of the target units of the single-purpose radiation sources.

3. The multiradiation generation apparatus according to claim 2, wherein the target unit of the dual-purpose radiation source has higher heat release properties than those of each of the target units of the single-purpose radiation sources.

4. The multiradiation generation apparatus according to claim 2,
wherein the target unit includes a substrate and a target layer which is formed on a side of the substrate on the side facing the electron source, and
wherein the substrate of the target unit of the dual-purpose radiation source is thicker than the substrate of each of the target units of the single-purpose radiation sources.

5. The multiradiation generation apparatus according to claim 2,
wherein the target unit includes a substrate and a target layer which is formed on a side of the substrate on the side facing the electron source, and
wherein the substrate of the target unit of the dual-purpose radiation source has a larger diameter than that of each of the substrates of the target units of the single-purpose radiation sources.

6. The multiradiation generation apparatus according to claim 2,
wherein the target unit of the dual-purpose radiation source is arranged with an inclination with respect to a direction in which the electrons are caused to be incident, and
wherein each of the target units of the single-purpose radiation sources is arranged perpendicularly with respect to the direction in which the electrons are caused to be incident.

7. The multiradiation generation apparatus according to claim 1,
wherein the passage hole of the shield is arranged on the side of the electron source and passes the electrons, and
wherein the emission hole of the shield is arranged on the opposite side of the electron source and allows emission of radiation generated by the target unit to a predetermined region.

8. The multiradiation generation apparatus according to claim 7, wherein the shield of the dual-purpose radiation source is thicker than each of the shields of the single-purpose radiation sources in a direction perpendicular to the row of the target units and a direction in which the electrons are caused to be incident.

9. The multiradiation generation apparatus according to claim 7, wherein a heat-release fin is connected to the shield of the dual-purpose radiation source.

10. The multiradiation generation apparatus according to claim 7, wherein the shields of the radiation sources are integrally formed.

11. A radiation imaging system comprising:
the multiradiation generation apparatus according to claim 1;
a radiation detection apparatus configured to detect radiation that has been emitted from the multiradiation generation apparatus and has passed through an object; and
a system control apparatus configured to perform cooperation control over the radiation generation apparatus and the radiation detection apparatus.

12. The radiation imaging system according to claim 11, wherein the radiation imaging system has a tomosynthesis imaging mode in which radiation is sequentially emitted from the radiation sources arranged in a row, and a non-tomosynthesis imaging mode in which radiation is emitted only from the dual-purpose radiation source.

13. The radiation imaging system according to claim 12, wherein the system control apparatus performs control so that a first acceleration voltage is applied between the electron source and the target unit of each of the radiation sources in the tomosynthesis imaging mode, and a second acceleration voltage different from the first acceleration voltage is applied between the electron source and the target unit of the dual-purpose radiation source in the non-tomosynthesis imaging mode.

14. A multi X-ray generation apparatus comprising:
a cathode array having a plurality of electron emitting sources each of which is aligned in a sequential manner;
an anode array having a shield member having a plurality of apertures corresponding to the electron emitting source and a plurality of targets each of which is secured to the corresponding aperture; and
a vacuum envelope having a cavity for storing the cathode array therein and an opening for securing the anode array,
wherein the plurality of targets includes a dual-purpose target used for both tomosynthesis imaging and non-tomosynthesis imaging and a plurality of single-purpose targets used only for tomosynthesis imaging, and
wherein a distance between a focal spot on the dual-purpose target and the shield member is shorter than a distance between a focal spot on any one of the plurality of single-purpose targets and the shield member such that a thermal transmittance from the dual-purpose target to the shield member is higher than a thermal transmittance from any one of the plurality of single-purpose targets to the shield member.

15. The multi X-ray generation apparatus according to claim 14, wherein, when electrons are irradiated under the same conditions, an electron irradiated surface of the dual-purpose target is configured to have a smaller temperature increase than that of each of the single-purpose targets.

16. The multi X-ray generation apparatus according to claim 15, wherein the dual-purpose target has higher heat release properties than those of each of the single-purpose targets.

17. The multi X-ray generation apparatus according to claim 15,
wherein the plurality of targets includes a substrate and a target layer which is formed on a side of the substrate on the side facing the electron emitting source, and
wherein the substrate of the dual-purpose target is thicker than the substrate of each of the single-purpose targets.

18. The multi X-ray generation apparatus according to claim 15,
wherein the plurality of targets includes a substrate and a target layer which is formed on a side of the substrate on the side facing the electron emitting source, and
wherein the substrate of the dual-purpose target has a larger diameter than that of each of the substrates of the single-purpose targets.

19. The multi X-ray generation apparatus according to claim 15,
wherein the dual-purpose target is arranged with an inclination with respect to a direction in which the electrons are caused to be incident, and
wherein each of the single-purpose targets is arranged perpendicularly with respect to the direction in which the electrons are caused to be incident.

20. The multi X-ray generation apparatus according to claim 14,
wherein the plurality of apertures of the shield member allow passing of the electrons and allows emission of radiation generated by the plurality of targets to a predetermined region.

21. The multi X-ray generation apparatus according to claim 20, wherein the shield member of the dual-purpose target is thicker than each of the shield members of the single-purpose targets in a direction perpendicular to the row of the targets and a direction in which the electrons are caused to be incident.

22. The multi X-ray generation apparatus according to claim 20, wherein a heat-release fin is connected to the shield member of the dual-purpose target.

23. The multi X-ray generation apparatus according to claim 20, wherein the shield member is integrally formed.

24. A radiation imaging system comprising:
the multi X-ray generation apparatus according to claim 14;
a radiation detection apparatus configured to detect radiation that has been emitted from the multi X-ray generation apparatus and has passed through an object; and
a system control apparatus configured to perform cooperation control over the X-ray generation apparatus and the radiation detection apparatus.

25. The radiation imaging system according to claim 24, wherein the radiation imaging system has a tomosynthesis imaging mode in which radiation is sequentially emitted from the electron emitting sources arranged in a row, and a non-tomosynthesis imaging mode in which radiation is emitted only from the dual-purpose target.

26. The radiation imaging system according to claim 25, wherein the system control apparatus performs control so that a first acceleration voltage is applied between the electron emitting source and the plurality of targets in the tomosynthesis imaging mode, and a second acceleration voltage different from the first acceleration voltage is applied between the electron emitting source and the dual-purpose target in the non-tomosynthesis imaging mode.

* * * * *